United States Patent [19]

Lunenfeld et al.

[11] Patent Number: 5,175,111
[45] Date of Patent: Dec. 29, 1992

[54] MANAGEMENT OF INFERTILITY

[75] Inventors: Bruno Lunenfeld, Tel-Aviv; Yeheskel Menashe, Or Akiva, both of Israel

[73] Assignee: Applied Research Systems ARS Holding N.V., Curacao, Netherlands Antilles

[21] Appl. No.: 592,441

[22] Filed: Oct. 1, 1990

[30] Foreign Application Priority Data

Oct. 2, 1989 [GB] United Kingdom ............... 8922137

[51] Int. Cl.$^5$ .......................................... G01N 33/543
[52] U.S. Cl. .................................... 436/518; 436/510; 436/818; 436/817; 424/9; 128/630
[58] Field of Search ............... 128/898, 760, 632, 630; 436/906, 510, 518, 817, 818; 514/401; 424/9

[56] References Cited

U.S. PATENT DOCUMENTS

| | | | |
|---|---|---|---|
| 4,182,773 | 1/1980 | Bartmann et al. | 514/530 |
| 4,296,121 | 10/1981 | Bartmann et al. | 514/438 |
| 4,910,215 | 3/1990 | Müller | 514/401 |
| 5,091,170 | 2/1992 | Navot | 424/9 |

FOREIGN PATENT DOCUMENTS 1036591 7/1962 United Kingdom ............... 436/510

OTHER PUBLICATIONS

Tsai, T. H., et al., "Teratologic and Reproductive Studies of Lofexidine", (1982), pp. 962–966.
Weppelman, R. M. et al., "Antifertility effects of clonidine in laying hens", (1981), pp. 995–997.
Chemical Abstracts, vol. 106, No. 11, Mar. 16, 1987, Abstract No. 79035.
Fertility and Sterility, vol. 53, No. 3, Mar. 1990, pp. 432–435.
Chemical Abstracts, vol. 90, No. 1, Jan. 1, 1979, Abstract No. 411.
Biological Abstracts, vol. 83, No. 11, 1987, Abstract No. 111344.
The Treatment of Fertility Disturbances with Special Reference to the use of Human Gonadotropins, E. Rabua et al, Fertility Disturbances in Men and Women, pp. 508–540 (Karger, Basel 1971).

Primary Examiner—C. Fred Rosenbaum
Assistant Examiner—Mark O. Polutta
Attorney, Agent, or Firm—Foley & Lardner

[57] ABSTRACT

A method for determining whether an infertile patient is likely to benefit from combined GH/gonadotropin or GHRH/gonadotropin therapy comprising the steps of (1) administering a predetermined dose of clonidine or a pharmaceutically acceptable derivative thereof to the patient; (2) monitoring the blood level of GH following the administration of clonidine or a derivative thereof; and (3) detecting whether the peak blood level of GH is above a predetermined level.

9 Claims, No Drawings

MANAGEMENT OF INFERTILITY

The present invention is concerned with the management of infertility, and more particularly is concerned with a test for improving and rationalising such treatment.

Human female infertility is an intractable problem, often having its roots in an inbalance in the endocrine system. In recent years, a large measure of success has been achieved in treating human female infertility by use of gonadotropin stimulation of the ovaries. A number of gonadotropin stimulation protocols have been devised, one of the most successful being the combined use of FSH (follicle stimulating hormone) and LH (luteinising hormone). A mixture of these two hormones is known as hMG (human menopausal gonadotropin).

However, treatment with hMG is by no means always successful, and on the one hand it would be desirable to increase the percentage of pregnancies resulting from the treatment. On the other hand, gonadotropin therapy must be performed with care since over-stimulation of the ovaries can lead to superovulation and multiple pregnancies (twins, triplets, quadruplets etc.).

It is known that the effect of gonadotropin therapy can sometimes be improved by the addition of GH (human growth hormone) or GHRH (growth hormone releasing hormone) to the therapeutic regimen. This combined treatment apparently has the effect of making the ovaries more sensitive to gonadotropin stimulation. However, even this combined therapy is not effective with all anovulatory patients. Since GH and GHRH are costly, it would be highly desirable to have some means of detecting those patients on which combined GH/gonadotropin or GHRH/gonadotropin therapy is likely to be an improvement on gonadotropin treatment alone. The availability of such a test would enable a more rapid and effective treatment regimen to be used; would avoid unnecessary use of GH or GHRH on patients for whom it would be of no additional benefit; and would avoid the psychological distress caused by prolonged and varied treatment on an empirical basis.

We have now found that the level of GH reserve as measured by the clonidine test correlates well with ovarian response to gonadotropin therapy.

Thus in one aspect our invention provides a method for detecting whether an infertile female patient is likely to benefit from combined GH/gonadotropin or GHRH/gonadotropin therapy which comprises administering a predetermined dose of clonidine or a pharmaceutically acceptable derivative thereof to said patient; monitoring the blood level of GH after administration of said clonidine or derivative thereof; and detecting whether the peak blood level of GH is above a predetermined minimum value.

Patients whose blood level of GH is above said minimum value will be defined hereinafter as being "clonidine positive" while those whose GH blood level is below said minimum value will be referred to as "clonidine negative". The minimum value of the peak blood level is about 4 ng/ml.

Preferably, clonidine hydrochloride is administered orally at a dosage of about 0.25 to 0.6 mg, preferably about 0.3 mg.

In a further step, a patient who is clonidine negative is treated by combined GH and gonadotropin therapy, preferably GH/hMG therapy. It will be appreciated that GH may be administered as such or an appropriate release of GH from the pituitary may be triggered by administration of GHRH. If the latter therapy is contemplated, a further test may be performed by challenging the patient with GHRH alone e.g. at a dosage rate of about 1 μg/kg and measuring resultant blood levels of GH. If blood GH level does not rise strongly in response to GHRH stimulation, the patient has pituitary GH failure and will benefit only from GH/gonadotropin therapy. However if a positive response to GHRH is seen, the patient has hypothalamic GH failure (i.e. a failure by the hypothalamus to produce endogenous GHRH—stimulation of the pituitary). Such patients will benefit either from GHRH/gonadotropin or GH/gonadotropin therapy.

The aforementioned tests can be performed very quickly and infertility therapy can be started immediately on a rational basis, with an excellent chance of success. This represents a major advance in infertility treatment.

Instead of instituting combined GH/gonadotropin or GHRH/gonadotropin therapy in clonidine negative patients, it is also feasible to use higher doses of gonadotropins. This may achieve a similar effect, although in a clonidine positive patient it would of course result in a dangerous risk of superovulation. Thus by use of the clonidine test, the dosage of gonadotropins can be planned with more certainty.

It is important to note that the clonidine test for GH reserve appears to be a more effective indication of ovarian sensitivity to GH than other methods of inducing GH release, such as direct stimulation of the pituitary with GHRF, and arginine stimulation. This is a surprising result, and indicates that the three GH reserve tests are not biologically equivalent for purposes of controlling infertility treatment.

Another aspect of our invention is the use of clonidine to prepare a diagnostic composition for stimulating release of GH in an infertile female patient, to ascertain whether said patient will benefit from combined GH/gonadotropin or GHRH/gonadotropin therapy for infertility.

It will be appreciated that "clonidine" refers herein also to bioequivalent derivatives thereof, especially acid addition salts thereof such as the hydrochloride.

The experimental basis for our invention will now be described in detail.

MATERIALS AND METHODS

Twenty-five patients with cyclic spontaneous bleeding who were anovulatory as diagnosed by basal body temperature and persistent low progesterone levels seeking ovulation induction were enrolled in this study. They had no systemic diseases, were normoprolactinemic, their FSH, LH and GH levels were not elevated and they previously failed to conceive with clomiphene citrate (cc). Prior to hMG administration the height and weight of the patients were determined. On day 5 after spontaneous bleeding, clonidine HCl Tablets (Normopresan, Rafa, Israel) 0.150 mg ×2 Oral Dose were administered. Blood samples were taken at 0, 30, 60, 90 and 120 minutes, and GH levels were measured using a double antibody radioimmunoassay (RIA) kit provided by Diagnostic Products Corporation (DPC), Los Angeles, Calif.

The sensitivity of the assay was 1 ng/ml. The intra- and inter-assay coefficients of variations were 5% and 8%, respectively.

The GH responses to clonidine administration were arbitrarily classified as: 1) clonidine positive: Patients who reached GH levels>4 ng/ml; and 2) clonidine negative: when no increase in GH was observed or the peak level of GH did not exceed 4 ng/ml.

The arginine test was performed on the morning of day 5, following the last menstrual bleeding episode, and after an overnight fast. Arginine monohydrochloride (30 g) was dissolved in 500 ml of 0.45% saline solution. The final pH was 6.8. The solution was passed through a Seitz filter for sterilization, and was infused rapidly within 30 minutes through the anticubital vein. Blood samples were drawn just prior to the beginning of infusion, at 30 min. (at the end of the infusion period) at 60, 90 and 120 min. The samples were analyzed for glucose, insulin and GH.

The GH responses to arginine administration were classified as:
1) arginine positive: patients who reached peak GH levels>6 ng/ml
2) arginine negative: when GH peak levels did not exceed 5 ng/ml.

The GHRH test was performed by administering a single bolus of GHRH 1 μg/kg (Geref 50, Serono) in the morning after an overnight fast. Blood samples were drawn before, and at 5, 15, 30 and 60 min. after GHRH administration.

The GH responses to GHRH administration were classified as:
1) GRF positive: patients who reached peak GH levels>20 ng/ml
2) GRF equivocal: when GH peak levels were between 5 and 10 ng/ml
3) GRF negative: when GH levels did not exceed 2× base level.

Human menopausal gonadotropin (Pergonal, Teva, Israel; 75 IU FSH and 75 IU LH per ampoule), was administered according to our individually adjusted treatment protocol (Rabau E. Lunenfeld B. and Insler V.: The treatment of fertility disturbances with special reference to the use of human gonadotropins, In: "Fertility disturbances in men and women", Edited by C. A. Joel, Publishers S. Karger, Basel, 1971, p. 508). Treatment was started with 2 ampoules of hMG on day 5 following bleeding and dose levels were adjusted according to patients' response.

The treating physicians were not aware of the clonidine test results and the laboratory investigators did not know of the patient response. The treatment was monitored by serial serum oestradiol ($E_2$) measurements and follicular dimensions. Oestradiol was determined by a direct RIA provided by DPC. The sensitivity of the assay was 20 pg/ml.

The intra and inter-assay coefficient of variation were 7% and 10%, respectively. Ultrasonography was performed using an Elscint model ESI-1000 (Elscint, Haifa, Israel) vagina ultrasound transducer that produced pulse waves of 6.5 MHz or an abdominal transducer that produced 3.5 MHz.

Stimulation was continued until at least one follicle had a diameter> 15 mm and $E_2$ level was >399 pg/ml. Human chorionic gonadotropin (hCG) 10,000 IU (Chorigon, Teva, Israel,) was then administered to induce ovulation. This was followed by 10,000 IU and 5,000 IU, 24 hours and 48 hours later.

The results of the hMG therapy were classified into 3 groups for the purpose of this study: 1) Good response, a level 400 pg/ml of $E_2$ in the presence of one or more follicles >15 mm, on the last day of hMG therapy; 2) Inadequate response, no follicle >14 mm, on the last day of hMG therapy; and 3) Poor response, $E_2$ level below 90 pg/ml on the last day of hMG therapy.

The results of the clonidine test were then correlated to the number of hMG ampoules necessary to obtain follicular stimulation compatible with ovulation. Results were expressed as mean±standard error of mean (SEM) and statistical analysis was performed by the appropriate tests. P values<0.05 were considered as significant in this study.

Of the clonidine negative patients, 13 were then reinvestigated by both the arginine and the GRF test. The results of the different tests were then compared.

RESULTS

Of the 25 patients recruited to the study, 8 responded to clonidine with significant increase in GH (peak levels of 9.2±4.5 ng/ml) and were classified as clonidine positive and 17 showed little or no GH elevation in response to clonidine (2.04±1.2 ng/ml) and were considered as clonidine negative.

The mean age of the clonidine positive women was 29.1±2.1 years and of the clonidine negative patients 34.3±2 years. Although the mean was slightly higher in the clonidine negative patients, the difference was not significant (P>0.11). The mean body surface and weight (1.6±0.02 m$^2$ and 55.4±0.95 Kg) of the clonidine positive patients was not significantly different from that of the clonidine negative women (1.8±0.1 m$^2$ and 67±6.09 Kg).

The mean basal level of GH of 24 patients (the primary GH deficient patient was excluded from the calculation) 1.49±1.05 ng/ml. There was no significant difference in the basal levels of GH between the group that responded to clonidine (1.39±0.66 ng/ml) and the group which did not respond (1.58±1.24 ng/ml).

There was no significant difference in the basal levels of FSH between the group that responded to clonidine (4.6±1.8 ng/ml) and the group which did no respond (7.1±4.5 mIU/ml).

There was no significant difference in the basal levels of LH between the group that responded to clonidine (6.2±3.5 mIU/ml) and the group which did not respond (5.6±3.2 mIU/ml).

There was however a significant difference (p<0.05) in the basal levels of somatomedin-C between the group that responded to clonidine (29.8±4.6 nMl) and the group which did not respond (20.0±6.2 nMl).

All the clonidine positive patients had a good response to hMG. Of the clonidine negative patients, 10 had a good response and 7 had an "inadequate or poor response". There was a significant difference in the quality of response between the 2 groups (P<0.05 by the Fisher's exact probability test).

The total dose of hMG which evoked a good response in clonidine negative patients was 36.5±5.5 ampoules. (2737±413 IU, FSH and LH) and it was significantly greater (p<0.005) than in clonidine positive patients (11.6±1.3 ampoules or 870±98 IU, FSH and LH, FIG. 2). The mean daily effective dose of hMG which evoked a good response in clonidine negative patients was 227±24 IU FSH/LH (3±0.3 ampoules).

The mean daily effective dose of hMG which was necessary to evoke similar ovarian response, as expressed by $E_2$ levels and follicular development in clonidine positive patients was significantly lower, 123±13 IU, FSH/LH (P<0.005).

In the clonidine negative group there were 7 cases with poor response to hMG, expressed by either low $E_2$ level (<90 pg/ml) and or insufficient follicular development. Oestradiol levels <90 pg/ml (mean 67 pg/ml±18 pg/ml) following a total dose of 12 to 27 ampoules of hMG (mean 21±8 ampoules) were found in 5 women. The two other patients had an inadequate response to hMG. One attained $E_2$ level of 268 pg/ml with no follicles >12 mm in size, despite 75 ampoules of hMG. The second patient attained $E_2$ level of 595 pg/ml, however only one follicle of 10 mm was found despite 16 ampoules of hMG, and treatment was stopped.

One of the clonidine negative patients who responded poorly to hMG, ovulated and conceived in a subsequent cycle when the dose of hMG was increased from 16 to 27 ampoules.

Four of the clonidine negative patients conceived in a subsequent cycle when GH 4-12 IU was given on alternative days concomitant with hMG. The hMG dose in the ovulatory cycles was significantly smaller than in the previous cycles when hMG was given alone.

Of the 13 clonidine negative patients 8 had a positive response to GHRH. In 3 the response was equivocal and in 2 patients GRF did not evoke a GH response Peak values of GH reached 24.5±1.87 ng/ml at 30 min and was significantly higher (P<0.001) than that of the equivocal responders (6.9±1.8 ng/ml). The 2 GRF negative patients were known to be GH deficient. One had received GH treatment in the past for short stature due to GH deficiency.

All the 13 clonidine negative patients responded with an increase of insulin within 30 min following arginine infusion. However only 8 responded with a GH increase. Peak values of GH reached 10.4±4 ng/ml and were significantly higher (P<0.01) than the non-responders (1.7±0.4).

Of the 5 non responders, 3 had an equivocal GH response following GHRH and 2 were the GRF non responding GH deficient short stature patients.

The above results demonstrate that all the patients who responded to clonidine with elevation of GH responded normally to hMG therapy with a mean dose of 870±98 IU, FSH/LH. Patients who did not respond to clonidine with elevation of GH, either needed excessive amounts of gonadotropins (2373±413 IU FSH/LH) to obtain an acceptable response, or despite higher doses of hMG responded inadequately as expressed by either low oestradiol level, lack of sufficient follicular development or both.

It is of interest to note that one of the clonidine negative patients who responded poorly to hMG, ovulated and conceived in a subsequent cycle when the dose of hMG was increased. This seems to indicate that clonidine negative patients given excessive doses of gonadotropins may respond normally as expressed by ovulation and conception. The fact that 4 of the clonidine negative patients who so far were treated with the combined GH/hMG treatment regimen needed significantly less hMG than in the previous treatment cycles when hMG only was used, demonstrates that in patients with a deficient GH reserve, addition of GH to hMG increases ovarian sensitivity to gonadotropin stimulation, and reduces the amount of hMG necessary for normal follicular development.

However it also demonstrates that the modulating role of GH either directly or via the stimulation of growth factors, is only permissive and can be overcome by pharmacological doses of gonadotropins.

Comparison between the clonidine test and other parameters or tests to predict decreased ovarian sensitivity related to GH and or growth factors showed: Basal levels of somatomedin-C were significantly lower in the group of clonidine negative patients as compared to clonidine positive patients. However the range of values 12.7-31.0 nMl in the clonidine negative patients overlapped with the values of the clonidine positive patients (22.4-35.3 nMl). Thus basal levels of somatomedin-C do not permit a reliable differentiation, permitting selection of patients for higher hMG dosage or for combined hMG-GH or hMG-GRF therapy.

Since all but two patients responded to GHRH it can be concluded that except in pituitary GH deficiency (pituitary dwarfism) the GHRH test cannot differentiate between good and poor responders. It further demonstrates the Clonidine negative patients can have a pituitary capable of responding to GHRH.

Since only 5 of the 13 clonidine negative patients did not respond to arginine stimulation with an increase in GH, the arginine provocation test seems less effective as an indicator of ovarian sensitivity to gonadotropins, and as a tool to select patients for the combined GH/hMG therapy.

We claim:

1. A method for detecting whether an infertile female patient is likely to benefit from combined human growth hormone (GH) gonadotropin or growth hormone releasing hormone (GHRH) gonadotropin therapy which comprises administering a predetermined dose of clonidine or a pharmaceutically acceptable derivative thereof to said patient; monitoring the blood level of GH following administration of said clonidine or derivative thereof; and detecting whether the peak blood level of GH is above a predetermined minimum value.

2. A method according to claim 1, wherein clonidine hydrochloride is administered.

3. A method according to claim 2, wherein clonidine hydrochloride is administered orally at a dosage of between 0.25 to 0.6 mg, preferably about 0.3 mg.

4. A method according to claim 1, wherein clonidine or a derivative thereof is administered after a predetermined time interval following the onset of spontaneous menstrual bleeding.

5. A method according to claim 1, wherein said blood level of GH is detected by way of radioimmunoassay (RIA).

6. A method according to claim 1, wherein the said predetermined minimum value of the peak blook level of GH is about 4 ng/ml.

7. A method according to claim 1, wherein said patient having a peak blood level of GH below the predetermined value is further assessed for likely benefit from combined GH/gonadotropin therapy and not from GHRH/gonadotropin therapy by the steps of administering a predetermined dose of GHRH to the patient; monitoring the blood level of GH following administration of said GHRH and detecting the absence of a rise in the blood GH level above a predetermined peak level.

8. A method according to claim 7, wherein said predetermined dose of GHRH is about 1 µg/kg.

9. A method according to claim 8, wherein said predetermined peak level is less than about 2× base level.

* * * * *